United States Patent [19]

Higgins et al.

[11] Patent Number: 4,485,666
[45] Date of Patent: Dec. 4, 1984

[54] GAS ANALYZER

[75] Inventors: John C. Higgins, Edinburgh; Harvie R. C. Wright, Livingston; David Trainer, Prestwick, all of Scotland

[73] Assignee: Coal Industry (Patents) Limited, London, England

[21] Appl. No.: 409,149

[22] Filed: Aug. 18, 1982

[30] Foreign Application Priority Data

Sep. 11, 1981 [GB] United Kingdom ............... 8127537

[51] Int. Cl.³ .................. G01N 27/16; G01N 27/26
[52] U.S. Cl. .............................. 73/23; 204/409; 422/94
[58] Field of Search ............. 73/23; 204/406, 409, 204/424, 431, 432; 422/94, 98; 340/632, 633

[56] References Cited

U.S. PATENT DOCUMENTS

| 3,237,181 | 2/1966 | Palmer | 340/633 |
| 3,266,293 | 8/1966 | Hubner | 73/23 |
| 3,519,391 | 7/1970 | Winter et al. | 340/633 |
| 4,128,458 | 12/1978 | Obiaya | 422/94 |
| 4,189,725 | 2/1980 | Rowland | 73/23 |

FOREIGN PATENT DOCUMENTS

| 1334286 | 10/1973 | United Kingdom . |
| 1450776 | 9/1976 | United Kingdom . |
| 1511467 | 5/1978 | United Kingdom . |
| 1575767 | 9/1980 | United Kingdom . |
| 1584830 | 2/1981 | United Kingdom . |

Primary Examiner—Stephen A. Kreitman
Attorney, Agent, or Firm—Stevens, Davis, Miller & Mosher

[57] ABSTRACT

A portable gas analyzer uses a pump to take a gas sample and pump it through a carbon monoxide sensing cell, an oxygen-sensing cell and a methane-sensing pellister. Concentrations of these gases are displayed continuously on LCD displays. The gas analyzer is particularly useful in underground coal mines and offers the possibility of replacing many different gas analyzers with a simple convenient apparatus which gives continuous readings of all the critical gas concentrations.

4 Claims, 1 Drawing Figure

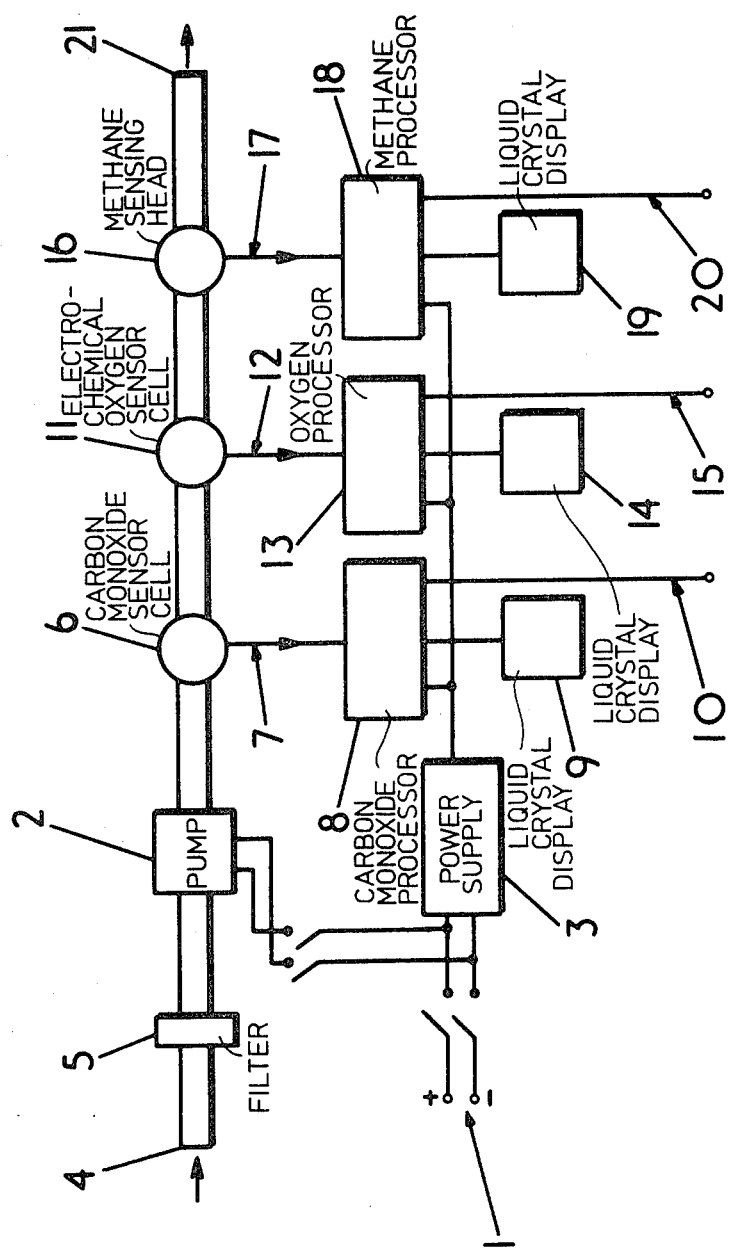

GAS ANALYZER

This invention concerns an improved gas analyser in which a plurality of gases are continuously sensed, especially suitable for use in underground coal mines.

It is known to use gas sensors which determine the amount of a particular pre-selected gas in an atmosphere. For example, it is known to use a carbon monoxide-sensing electrochemical cell, or an infra-red analyser, for determining the concentration of carbon monoxide in the atmosphere of a coal mine. It is also known to analyse mine atmospheres for methane, by passing the methane-containing atmosphere over a heated pellistor which catalyses the oxidation of methane. Oxygen sensors, generally based upon an electrochemical cell, are also known. Such gas sensors may be portable, that is may be carried around by a man, and placed at an appropriate position underground, or they may be part of a fixed analysing unit on the surface as part of a "tube-bundle" system. The "tube-bundle" system is in quite widespread use within British coal mines, and consists of a surface monitoring station and a collection of long tubes which are led to various important parts of the mine. The atmosphere at these parts can be analysed by drawing off a sample and pumping it to the surface station. Although this system is capable of giving accurate results there may be problems in practice from leaking tubes or from the delay in passage of samples from the various parts of the mine; the rate at which a complete preprogrammed cycle of sampling and analysis is completed may mean a delay of one or two hours in detecting an occurrence which has led to a change in the mine atmosphere. The system used for determining carbon monoxide involves infra-red spectrometry and although it is accurate it is bulky, costly and completely unsuitable for use underground in a mine environment.

There has not been, as far as we are aware, any commercially marketed instrument for use underground which is portable and capable of determining more than one component of a gas mixture simultaneously. It is an aim of the present invention to provide an improved gas analyser capable of being carried to an appropriate point in an underground coal mine, and there used in one of a number of different modes.

Accordingly, the present invention provides a portable gas analyser capable of simultaneously determining carbon monoxide, oxygen and methane, comprising a single gas inlet, means for drawing a sample of gas through the inlet and feeding said sample successively through first, second and third gas analysing means to simultaneously determine the concentration of carbon monoxide, oxygen and methane and means for simultaneously displaying and/or transmitting and/or recording the determined concentrations of the gases.

There exist suitable commercial electrochemical cells or the like which provide acceptable accuracy with small size and light weight and these are preferred for use in the present invention. For example, to analyse carbon monoxide, an electrochemical cell may be used; such a cell may be of the three electrode or of a two electrode type. One suitable cell is manufactored by Interscan Corporation of Chatsworth, California, another is manufactured by City Technology Limited of London. For oxygen, it is suitable to use another electrochemical cell, such as the oxygen sensor manufactured by City Technology Limited. For methane, however, it is preferred to use a pellistor of known type; suitable pellistors are included in existing methane monitors such as those manufactured by English Electric Valve Co. of Chelmsford, Essex, England. Since the pellistor type of methane sensor results in the consumption of oxygen and the production of carbon dioxide, it is preferred to arrange the gas analysing means to have methane as the last gas to be analysed, to avoid the risk of inaccurate results for the other gases.

Preferably, a small pump is used to draw gas samples into the analyser. Initial tests indicate that a gas flow rate of 1,000 cc/min is suitable, but this may of course be varied according to the requirements of the user and the various gas analysing means chosen. A suitable pump is the Brey "Series G" Rotary vane type, powered by an "Escap" motor; this motor is a proven design and has been used widely underground in the Gravimetric Dust Sampler marketed by C. F. Casella & Co. Ltd. It is also preferred to include a filter to remove dust or other particulates before analysis of the gas sample; for example a replaceable glass fibre paper membrane filter of 5 micron nominal aperture may be mounted before the pump.

Most existing single gas analysers rely upon diffusion of the sample gas to the gas analysing means, such as to the sensing electrode of an electrochemical cell. In the present invention, a positive gas flow is maintained. Not only does this permit slightly more rapid response to changing conditions and permits the analysis in successive analysing means but also permits the use of a gas sampling probe. A gas sampling probe is preferred for certain investigative uses, as it can more accurately locate the major source of a particular gas and is considerably more convenient for use than offering up the instrument to the gas source.

Preferably, the concentration of the gases being sensed are continuously displayed as percentages of the atmosphere, on meters or more preferably on a digital display such as a solid-state LCD or LED display. Preferably, the analyser also provides output signals for each gas concentration; such ouput signals are conveniently of suitable characteristics to be fed to a complete electronic mine monitoring system such as that known as "MINOS" which is used increasingly in British coal mine. The analyser may include an alarm facility activated if methane, oxygen or carbon monoxide levels should fall into predetermined ranges, but this may be inappropriate if probing is done, since there are often localised pockets of gases which are nominally dangerous but not so in aggregate.

In a preferred embodiment of the invention, the analyser is powered by a rechargeable battery and uses circuitry operating at low voltage and which is current-stabilised so that rather than relying upon the power cell characteristic of a relatively constant voltage during the discharge which gives a voltage "plateau", a much more stable performance can be achieved. Such circuitry preferably provides a battery cut-out whenever the +ve or −ve voltage falls below a pre-selected level to prevent damage to the cells caused by excessive discharge.

The gas analyser of the invention can be used in a number of different ways . Because it is portable, it can be carried by someone as an aid to inspection, especially for the detection of carbon monoxide which is an indication of spontaneous combustion, and for the detection of methane emissions and the detection of oxygen deficiency. Thus, the analyser provides a means to pinpoint problem areas for early preventative action and in the case of emergency conditions gives a rapid read-out of the atmospheric components which are essential knowledge. The ability to display the concentrations of these gases on one instrument, rather than the three which have until now been used, is of very great importance in a practical sense. Such a portable analyser may, of course, be left in position for a length of time; suitably it is powered by a battery capable of giving 20 hours or more of continuous operation.

The analyser may also be used at a fixed or semi-permanent site, operating off a main power supply with battery back-up. For example, an analyser can form part of the equipment of a control centre for coordinating rescue or other emergency work.

Another role for the gas analyser is at a "permanent" site, for example adjacent to a coal face, at which the analyser is supplied with samples through tubes led directly from sampling points to the analyser. Such an installation would provide a local alternative to a complete tube-bundle system. The relative short length of tubes, and the reduced number of tubes would avoid many of the problems experienced by the tube-bundle system and permit easy replacement of damaged tubes. In such a case, the analyser would be used to generate signals which were transmitted to the surface for monitoring conditions, and would offer faster response times.

The invention will now be described with reference to the accompanying drawing which is a schematic system diagram of an analyser according to the invention.

The analyser is powered by a battery 1, of rechargeable Ni-Cad 4×1.2 V cells, which operates a pump 2, through a switchable connection and supplies power to a power supply unit 3, which provides a stabilised voltage output. A gas inlet 4, which may be in the form of an aperture on the analyser or may consist of a flexible sampling tube to be used on a probe or the like, serves to draw on atmosphere to be analysed into the analyser by means of the pump 2. The incoming gases are drawn by the pump at a rate of 1,000 cc/min through a 5 micron nominal aperture glass fibre paper in a filter unit 5, to remove particulates. The gases then pass through the pump into a carbon monoxide sensor cell 6, of known type. The output from the cell is portrayed as 7, and is processed in a carbon monoxide module 8, which converts the cell output into a signal indicative of the percentage concentration of carbon monoxide in the sampled gases, and which is used in conjunction with a conventional liquid crystal display unit 9, so that concentration is directly displayed. The signal is also converted into an analogue output 10, in the 0.4–2.0 V range, which is suitable for supply to a centralised data processing installation (not shown).

The gases are continuously passed through the carbon monoxide cell 6 to an electrochemical oxygen sensor cell 11, of known type. The ouput 12 from the oxygen cell is processed in an oxygen module 13, to give a direct reading of oxygen concentration of LCD display 14, and an analogue output 15.

After the oxygen detection, the gases are passed to a methane sensing head 16, of catalytic pellistor type, in which the methane is catalytically oxidised. The output 17, from the sensing head is passed to a methane module 18, for processing to a direct concentration signal for display on LCD display 19, and an analogue output 20. The gas is then exhausted through a gas outlet 21.

No correction of the output signals is required to take account of the prior history of the gas sample, but as is conventional, it is suitable to calibrate the analyser using a test gas of known compositions. The analyser can be constructed inside a sturdy carrying case (not shown) for protection of the analyser from the mining environment, and tests have shown that an analyser of good and reliable performance results. The analyser is easily carried and operated and provides for the first time simultaneous measurement of critical gas concentrations in underground coal mines.

We claim:

1. A portable gas analyser capable of simultaneously determining carbon monoxide, oxygen and methane, comprising a single gas inlet, feeding means connecting with said inlet, first, second and third gas analysing means each disposed along a single gas path, for deriving a signal indicative of the concentration of one of the gases carbon monoxide, oxygen and methane, and connecting with the inlet, said first and second analysing means each comprising an electrochemical cell and said third analysing means comprising a pellistor, said feeding means comprising means for drawing a sample of gas through the inlet and feeding it successively through said first, second and third gas analysing means, and means for continuously displaying and/or transmitting and/or recording the concentrations of said gases, derived from the signal from each gas analysing means.

2. An analyser as claimed in claim 1, comprising also a filter to remove particulates in a gas sample before contact with an analysing means.

3. An analyser as claimed in claim 1, comprising also a gas sampling probe connected to the inlet.

4. An analyser as claimed in claim 1, further comprising means for transmitting output signals for each gas concentration to an electronic mine monitoring system.

* * * * *